United States Patent
Root et al.

(10) Patent No.: US 11,279,510 B2
(45) Date of Patent: *Mar. 22, 2022

(54) SYSTEM AND METHOD FOR FREEZE-DRYING AND PACKAGING

(71) Applicant: Teleflex Life Sciences Limited, Valletta (MT)

(72) Inventors: Howard Root, Excelsior, MN (US); Stephen Anthony Penegor, Watertown, MN (US); James A. Murto, Maple Grove, MN (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

This patent is subject to a terminal disclaimer.

(21) Appl. No.: 17/079,790

(22) Filed: Oct. 26, 2020

(65) Prior Publication Data

US 2021/0039820 A1    Feb. 11, 2021

Related U.S. Application Data

(60) Continuation of application No. 16/386,026, filed on Apr. 16, 2019, now Pat. No. 10,882,654, which is a
(Continued)

(51) Int. Cl.
*B65B 63/08* (2006.01)
*B65D 81/24* (2006.01)
(Continued)

(52) U.S. Cl.
CPC ............... *B65B 63/08* (2013.01); *A61J 1/10* (2013.01); *A61J 1/1475* (2013.01); *A61J 1/2093* (2013.01);
(Continued)

(58) Field of Classification Search
CPC .......... B65B 63/08; B65B 3/003; B65B 7/02; B65B 51/225; B65C 1/02; B65D 81/245;
(Continued)

(56) References Cited

U.S. PATENT DOCUMENTS 1,504,225 A  *  8/1924  Fitzgerald ............... C08L 89/06
                                                        106/124.5
2,767,117 A  * 10/1956  Crawley ................. A61K 39/17
                                                        424/214.1
(Continued)

FOREIGN PATENT DOCUMENTS

CN       203284363 U    11/2013
DE       102013003851    3/2014
(Continued)

OTHER PUBLICATIONS

European Search Report dated Jul. 17, 2020 in European Application No. 20159141.9.

*Primary Examiner* — Stephen M Gravini
(74) *Attorney, Agent, or Firm* — Gregory W. Smock

(57) ABSTRACT

A system and method for protecting biological or other material from contamination through the steps of filling, freeze-drying, packaging, storing and use are disclosed. A system can include a flexible container, a membrane configured to transmit air or solvent vapor out of the flexible container, and a membrane frame supporting the membrane and engaged with at least one column member. The at least one column member can be configured to maintain the membrane and the membrane frame a spaced distance from one or more contents received within the flexible container. Upon application of a downward force, the at least one column member can assume a collapsed configuration. A method can include inserting a biological material, for example, into a flexible container, freeze-drying the biological material, moving the freeze-dried biological material to
(Continued)

a portion of the flexible container that includes at least one port, and sealing the biological material within the portion.

20 Claims, 9 Drawing Sheets

Related U.S. Application Data division of application No. 15/399,643, filed on Jan. 5, 2017, now Pat. No. 10,377,520, which is a division of application No. 14/553,722, filed on Nov. 25, 2014, now Pat. No. 9,561,893.

(60) Provisional application No. 61/912,281, filed on Dec. 5, 2013.

(51) Int. Cl.
  *A61J 1/10* (2006.01)
  *A61J 1/14* (2006.01)
  *A61J 1/20* (2006.01)
  *B65B 3/00* (2006.01)
  *A61M 5/14* (2006.01)
  *B65B 7/02* (2006.01)
  *B65B 51/22* (2006.01)
  *B65C 1/02* (2006.01)

(52) U.S. Cl.
  CPC ............ *A61M 5/14* (2013.01); *B65B 3/003* (2013.01); *B65B 7/02* (2013.01); *B65B 51/225* (2013.01); *B65C 1/02* (2013.01); *B65D 81/245* (2013.01); *A61M 2202/0415* (2013.01)

(58) Field of Classification Search
  CPC .... A61M 2202/0415; A61M 5/14; A61J 1/10; A61J 1/2093; F26B 5/00; F26B 5/06
  USPC .......................................................... 34/92
  See application file for complete search history.

(56) References Cited

U.S. PATENT DOCUMENTS

| | | | |
|---|---|---|---|
| 3,375,824 A * | 4/1968 | Krakauer | A61J 1/10 604/82 |
| 4,024,648 A | 5/1977 | Bender | |
| 4,218,321 A * | 8/1980 | Sasaki | A61M 1/3679 210/259 |
| 4,335,770 A | 6/1982 | Kulle et al. | |
| 4,453,320 A | 6/1984 | Zimmermann et al. | |
| 4,707,966 A | 11/1987 | Weiler et al. | |
| 4,813,210 A | 3/1989 | Masuda et al. | |
| 4,973,327 A * | 11/1990 | Goodrich, Jr. | F26B 5/06 604/408 |
| 4,994,057 A | 2/1991 | Carmen et al. | |
| 5,174,042 A | 12/1992 | Tomizawa et al. | |
| 5,257,983 A * | 11/1993 | Garyantes | F26B 25/16 604/403 |
| 5,309,649 A | 5/1994 | Bergmann et al. | |
| 5,514,123 A | 5/1996 | Adolf et al. | |
| 5,596,814 A | 1/1997 | Zingle et al. | |
| 5,894,949 A | 4/1999 | Taskis et al. | |
| 5,937,536 A | 8/1999 | Kieselbach et al. | |
| 5,958,778 A | 9/1999 | Kidd | |
| 6,375,028 B1 | 4/2002 | Smith | |
| 6,381,870 B1 | 5/2002 | Kohlman et al. | |
| 6,517,526 B1 | 2/2003 | Tamari | |
| 6,764,481 B1 | 7/2004 | Inada et al. | |
| 6,773,425 B1 | 8/2004 | Tamari | |
| 6,981,337 B2 | 1/2006 | Jones et al. | |
| 7,363,726 B2 | 4/2008 | Wang et al. | |
| 7,776,022 B2 | 8/2010 | McCarthy et al. | |
| 7,966,746 B2 | 6/2011 | Py | |
| 8,013,022 B2 | 9/2011 | DeAngelo et al. | |
| 8,076,034 B1 | 12/2011 | Lassila et al. | |
| 8,449,520 B2 | 5/2013 | Pepper et al. | |
| 8,512,428 B2 | 8/2013 | Ueki et al. | |
| 8,518,452 B2 | 8/2013 | Bjornstrup et al. | |
| 8,555,520 B2 | 10/2013 | Hedberg | |
| 9,347,707 B2 | 5/2016 | Struschka et al. | |
| 9,561,893 B2 * | 2/2017 | Root | A61J 1/1475 |
| 9,739,532 B2 | 8/2017 | Baugh et al. | |
| 9,796,273 B2 | 10/2017 | Ragazzini | |
| 9,801,784 B2 | 10/2017 | Yoshida et al. | |
| 9,863,699 B2 | 1/2018 | Corbin et al. | |
| 9,863,700 B2 | 1/2018 | Pedersen et al. | |
| 9,863,701 B2 | 1/2018 | Robinson | |
| 9,931,458 B1 | 4/2018 | Naro | |
| 10,300,444 B2 | 5/2019 | Prytz | |
| 10,377,520 B2 | 8/2019 | Root et al. | |
| 10,806,665 B2 | 10/2020 | Murto et al. | |
| 10,882,654 B2 * | 1/2021 | Root | B65B 3/003 |
| 2007/0219524 A1 | 9/2007 | Burnouf et al. | |
| 2008/0234654 A1 | 9/2008 | McCarthy et al. | |
| 2008/0256822 A1 | 10/2008 | Suzuki et al. | |
| 2009/0107001 A1 | 4/2009 | McCarthy | |
| 2009/0113753 A1 | 5/2009 | Pepper et al. | |
| 2009/0325771 A1 | 12/2009 | Inoue et al. | |
| 2014/0360891 A1 | 12/2014 | Kline et al. | |
| 2015/0158652 A1 | 6/2015 | Root et al. | |
| 2015/0231031 A1 | 8/2015 | Hayakawa et al. | |
| 2015/0354894 A1 | 12/2015 | Corbin et al. | |
| 2017/0113824 A1 | 4/2017 | Root et al. | |
| 2017/0203871 A1 | 7/2017 | Murto et al. | |
| 2019/0241300 A1 | 8/2019 | Root et al. | |
| 2020/0281858 A1 | 9/2020 | Murto et al. | |

FOREIGN PATENT DOCUMENTS

| | | |
|---|---|---|
| EP | 0854911 B1 | 11/2004 |
| JP | H07165252 A | 6/1995 |
| WO | 1995027180 A1 | 10/1995 |
| WO | 1996006018 A1 | 2/1996 |
| WO | 1996031748 A1 | 10/1996 |
| WO | 2008140747 A1 | 11/2008 |
| WO | 2010033169 A1 | 3/2010 |
| WO | 2015191599 A2 | 12/2015 |

* cited by examiner

SYSTEM AND METHOD FOR FREEZE-DRYING AND PACKAGING

CLAIM OF PRIORITY

This non-provisional patent application is a continuation of U.S. non-provisional patent application Ser. No. 16/386,026, issued as U.S. Pat. No. 10,882,654, entitled "SYSTEM AND METHOD FOR FREEZE-DRYING AND PACKAGING" and filed Apr. 16, 2019, which is a divisional application of U.S. non-provisional patent application Ser. No. 15/399,643, issued as U.S. Pat. No. 10,377,520, entitled "SYSTEM AND METHOD FOR FREEZE-DRYING AND PACKAGING" and filed on Jan. 5, 2017, which is a divisional application of U.S. non-provisional patent application Ser. No. 14/553,722, issued as U.S. Pat. No. 9,561,893, entitled "SYSTEM AND METHOD FOR FREEZE-DRYING AND PACKAGING" and filed on Nov. 25, 2014, which claims the benefit of priority under 35 U.S.C. § 119(e) to U.S. provisional patent application Ser. No. 61/912,281, entitled "SYSTEM AND METHOD FOR FREEZE-DRYING AND PACKAGING" and filed on Dec. 5, 2013, each of which is herein incorporated by reference in its entirety.

TECHNICAL FIELD

This patent document pertains to a system and method for, among other things, freeze-drying and packaging a material under aseptic or pathogen-reduced conditions.

BACKGROUND

Dry storage can increase the shelf life and convenience of biological material and its use. Lyophilization is a process for drying heat-sensitive substances, such as biological materials, by freezing the substances and then subliming the ice or other frozen solvent in a high vacuum.

It can be necessary to keep biological material free from micro-organisms and other contaminants to avoid decomposition of the material and to prevent possible infections when the material is used. Biological material can be exposed to contaminants during transportation to and from a freeze-dryer. As a result, the operating area in which freeze-drying is carried out can undergo sterilization treatment to minimize exposure of the biological material to contaminants. This adds to the labor and costs associated with freeze-drying.

Many freeze-drying processes involve placing open containers of biological material in the freeze-dryer. The containers remain open to the environment until the freeze-drying process is complete to allow a path for solvent vapor to be removed from the biological material. This practice exposes the biological material to potential contamination during the freeze-drying process. To minimize the opportunity for contamination during the freeze-drying process, the freeze-drying equipment can be sterilized using steam or chemicals before loading each new batch of biological material to be processed. This, too, adds to the labor and costs associated with freeze-drying.

Moreover, using existing systems and methods, freeze-dried biological material needs to be repackaged after being dried. This repackaging presents another opportunity to introduce contaminants into the biological material and further adds to the labor and costs associated with freeze-drying.

OVERVIEW

The present inventors recognize, among other things, that a need exists for a system and method that addresses the concerns of material contamination by freeze-drying equipment, the area surrounding the freeze-drying equipment, and the repackaging of freeze-dried product. The inventors recognize that biological material, such as blood plasma, is associated with a risk of contamination anytime it is exposed to the environment. The inventors also recognize that the system and method should be economical and practical on a production scale.

The present subject matter provides a system and method for protecting biological material, for example, from contamination through the steps of filling, freeze-drying, packaging, storing and use. A system can include a flexible container, a membrane configured to transmit air or solvent vapor out of the flexible container, and a membrane frame supporting the membrane and engaged with at least one column member. The at least one column member can be configured to maintain the membrane and the membrane frame a spaced distance from one or more contents receivable within the flexible container. Upon application of a downward force, the at least one column member can assume a collapsed configuration. A method can include inserting a biological material, for example, into a flexible container, freeze-drying the biological material, moving the freeze-dried biological material to a portion of the flexible container that includes at least one port, and sealing the biological material within the portion.

To further illustrate the system and method disclosed herein, a non-limiting list of examples is provided here:

In Example 1, a system can comprise a flexible container, a membrane, and a membrane frame engaged with at least one column member. The flexible container can be defined by a height of a first dimension and a width of a second dimension. The height can separate the flexible container into a first portion and a second portion at an intermediate location (e.g., the flexible container's midline). The membrane can be located within the first portion and can be configured to transmit air or solvent vapor out of, and resist liquid and contaminant passage into, the flexible container. The membrane frame can be coupled to both the membrane around its perimeter and a portion of the flexible container. The at least one column member can support the membrane and the membrane frame a spaced distance from one or more contents receivable within the flexible container.

In Example 2, the system of Example 1 can optionally be configured such that the at least one column member includes a plurality of column members. Each column member can be configured to change shape or position, relative to the membrane frame, upon application of a downward force to the membrane frame.

In Example 3, the system of Example 2 can optionally be configured such that each of the plurality of column members include at least one end engaged with the membrane frame and at least one end in contact with a surface of the flexible container.

In Example 4, the system of any one or any combination of Examples 2 or 3 can optionally be configured such that each of the plurality of column members defines a U-shape. The curvature of the U-shape can be engaged with the membrane frame.

In Example 5, the system of any one or any combination of Examples 1-4 is optionally configured such that the at least one column member is integral with the membrane frame.

In Example 6, the system of any one or any combination of Examples 1-5 can optionally be configured such that front and back sides of the flexible container are sealed to one another along an outer perimeter.

In Example 7, the system of Example 6 can optionally be configured such that a widthwise cross-section of the flexible container at the intermediate location defines an ellipsoid (or tear drop) shape.

In Example 8, the system of any one or any combination of Examples 1-7 can optionally be configured such that the flexible container includes a heat-sealable material.

In Example 9, the system of any one or any combination of Examples 1-8 can optionally be configured such that the membrane includes a material selected from a porous polymer, a woven polymeric fabric, a non-woven polymeric fabric, glass fiber or cellulose.

In Example 10, the system of Example 9 can optionally be configured such that the membrane includes a porous polymer material in the form of polytetrafluoroethylene.

In Example 11, the system of any one or any combination of Examples 1-10 can optionally further comprise a material entry port coupled to the flexible container within the first portion.

In Example 12, the system of Example 11 can optionally be configured such that the material entry port includes a tube extending from a first end, coupled to the flexible container, to a second end, couplable to a material source.

In Example 13, the system of any one or any combination of Examples 1-12 can optionally further comprise a reconstitution port coupled to an outer perimeter of the second portion of the flexible container and in fluid communication with an interior of the flexible container.

In Example 14, the system of any one or any combination of Examples 1-13 can optionally further comprise an application port coupled to an outer perimeter of the second portion of the flexible container and in fluid communication with an interior of the flexible container.

In Example 15, the system of any one or any combination of Examples 1-14 can optionally further comprise a single donor quantity of biological material within the flexible container.

In Example 16, the system of Example 15 can optionally be configured such that the single donor quantity of biological material includes blood plasma.

In Example 17, a method can comprise inserting a material into a flexible container including a membrane, freeze-drying the material, moving the freeze-dried material to a portion of the flexible container spaced from the membrane, and sealing the material within the portion of the flexible container. The membrane can be incorporated into a first container side and can be spaced from a second container side by a membrane frame and at least one column member.

In Example 18, the method of Example 17 can optionally further comprise applying a force to the membrane frame in a direction of the second container side.

In Example 19, the method of Example 18 can optionally be configured such that applying the force to the membrane frame in the direction of the second container side includes causing the at least one column to collapse relative to the membrane frame.

In Example 20, the method of any one or any combination of Examples 17-19 can optionally be configured such that sealing the material within the portion of the flexible container spaced from the membrane includes fluidly coupling a reconstitution port and the material.

In Example 21, the method of any one or any combination of Examples 17-20 can optionally be configured such that sealing the material within the portion of the flexible container spaced from the membrane includes fluidly coupling an application port and the material.

In Example 22, the method of any one or any combination of Examples 17-21 can optionally be configured such that sealing the material within the portion of the flexible container spaced from the membrane includes sealing across a width of the flexible container at a location in which the flexible container has capacity to receive at least 200 mL (milliliter) of a reconstitution liquid.

In Example 23, the method of Example 22 can optionally further comprise cutting through a formed seal and discarding a portion of the flexible container including the membrane, the membrane frame, and the least one column member.

In Example 24, the method of Example 23 can optionally further comprise forming a hang lumen through the remaining portion of the formed seal and cleaning the formed seal of material residue.

In Example 25, the method of any one or any combination of Examples 17-24 can optionally be configured such that freeze-drying the material in the flexible container includes freeze-drying blood plasma from a single donor or a pooling of donors.

In Example 26, the method of any one or any combination of Examples 17-25 can optionally further comprise labeling the portion of the flexible container in which the material is sealed.

In Example 27, the system or method of any one or any combination of Examples 1-26 can optionally be configured such that all features, components, operations, or other options recited are available to use or select from.

These and other examples and features of the present system or method will be set forth, at least in part, in the following Detailed Description. This Overview is intended to provide non-limiting examples of the present subject matter—it is not intended to provide an exclusive or exhaustive explanation. The Detailed Description below is included to provide further information about the present system or method.

BRIEF DESCRIPTION OF THE DRAWINGS

In the drawings, like numerals can be used to describe similar features and components throughout the several views. The drawings illustrate generally, by way of example, but not by way of limitation, various embodiments discussed in the present patent document.

Figure 1:
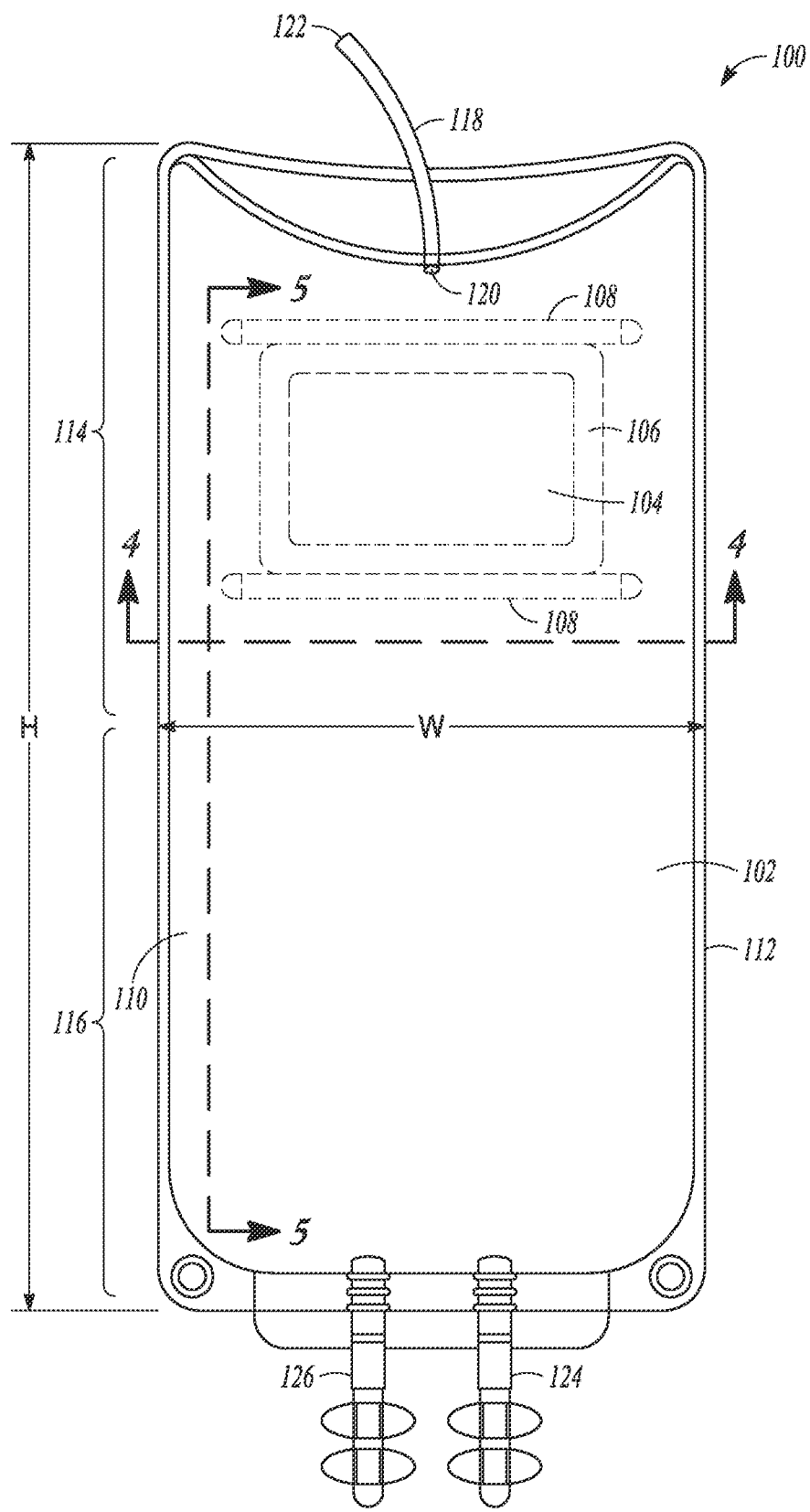
FIG. 1 illustrates a front elevational view of a system, as constructed in accordance with at least one embodiment.

The drawing figures are not necessarily to scale. Certain features and components may be shown exaggerated in scale or in schematic form and some details may not be shown in the interest of clarity and conciseness.

DETAILED DESCRIPTION

The present subject matter includes a method that protects material from contamination through the steps of filling, freeze-drying, packaging, storing and use. The method can include inserting a material into a flexible container, freeze-drying the material, moving the freeze-dried material to a portion of the flexible container that includes at least one port, and sealing the material within the portion. The method can be performed using a system as shown in the drawings and described herein. The system provides a practical, durable freeze-drying container and membrane that provide sufficient solvent vapor flow, resistance to breakage, wetting and abrasion, and aseptic barrier properties.

FIG. 1 illustrates a front elevational view of a system 100 configured to house a material, such as blood plasma from a single donor. The system can include a flexible container 102, a membrane 104, and a membrane frame 106 engaged with at least one column member 108 (shown in phantom).

The flexible container 102 can be used in a freeze-drying process. Biological material, for example, to be freeze-dried can be received within the flexible container 102 prior to lyophilization. The flexible container 102 can include a front side 110 and a back side 112, and can define a height H of a first dimension and a width W of a second dimension. The second dimension can be smaller than the first dimension. The terms "front" and "back," as used herein, refer to opposing walls of the flexible container 102 when it is placed on a freeze-dryer shelf with the membrane 104 facing upward. The height H can have an intermediate location (e.g., a midline) separating the flexible container into a first portion 114 and a second portion 116. In an example, the height H can be 6-18 inches, such as about 12 inches, and the width W can be 3-9 inches, such as about 6 inches.

The flexible container 102 can include a sealable material made of an inert medical grade plastic material, such as polyvinyl chloride (PVC), polypropylene or high density polypropylene, which is designed to resist tearing and puncturing that can be encountered in normal handling. The sealable material can be selected to be transparent to allow visual inspection of the biological material within the flexible container 102 and can be available in a variety of sizes, such as about 10 mL up to about 10 L. The front 110 and back 112 sides of the flexible container 102 can be heat-sealed or, alternatively, ultrasonically or radio-frequency (RF) welded to one another along an outer perimeter. This thermal sealing can be performed by Dravon Medical of Clackamas, Oreg.

The membrane 104 can be located within the first portion 114 of the flexible container 102 and can have a height of 1-3 inches, such as about 2 inches, and a width of 2-4 inches, such as about 3 inches. The membrane 104 can be configured to transmit air or solvent vapor out of, and resist liquid and contaminant passage into, the flexible container 102. The membrane's material can be selected for its combination of high aseptic barrier properties, high resistance to penetration and wetting by liquid water, and low resistance to solvent vapor flow. In an example, the material of the membrane 104 can include polytetrafluoroethylene (PTFE), which is available from Porex Corporation of Fairburn, Ga. The membrane 104 can be separate from, but attachable to, the front side 110 of the flexible container 102 by way of the membrane frame 106. In such examples, the membrane's material should have the ability to seal reliably to a material of the membrane frame 106.

The membrane frame 106 can be coupled to the membrane 104 around its perimeter and the front side 110 of the flexible container 102. The membrane frame 106 can provide strength and support to the membrane 104. The membrane frame 106 can be engaged with at least one collapsible column member 108 to prevent the membrane 104 from contacting biological material, for example, located within the flexible container 102, such as during the lyophilization process. The at least one column member 108 can be configured to support the membrane 104 and the membrane frame 106 a spaced distance from the back side 112 of the flexible container 102. In an example, the membrane frame 106 can be manufactured by Tauris Manufacturing of Minneapolis, Minn.

The system 100 can further include a plurality of ports to allow for the introduction or withdrawal of a material or substance into or out of the flexible container 102. A material entry port 118 can be coupled to the first portion 114 of the flexible container 102 and can be used to insert the biological material and, optionally, other materials within the container. In an example, one or more pH-adjusting substances can be inserted into the flexible container 102 and combined with the biological material to affect a predetermined pH value range in a reconstituted material solution. In an example, the material entry port can include a tube extending from a first end 120, coupled to the first side 110 of the flexible container 102, to a second end 122, couplable to a biological material source. A reconstitution port 124 and an application port 126 can be coupled to an outer perimeter of the second portion 116 of the flexible container 102 and can be in fluid communication with an interior of the container. These ports 124, 126 can allow a user to introduce a reconstitution (or rehydration) solution into the flexible container 102 and administer a rehydrated product (e.g., reconstituted biological material) to a patient, respectively, in an aseptic manner.

The system 100, including the flexible container 102, the membrane 104, the membrane frame 106 and the at least one column member 108, can be sterilized prior to use.

Figure 2:
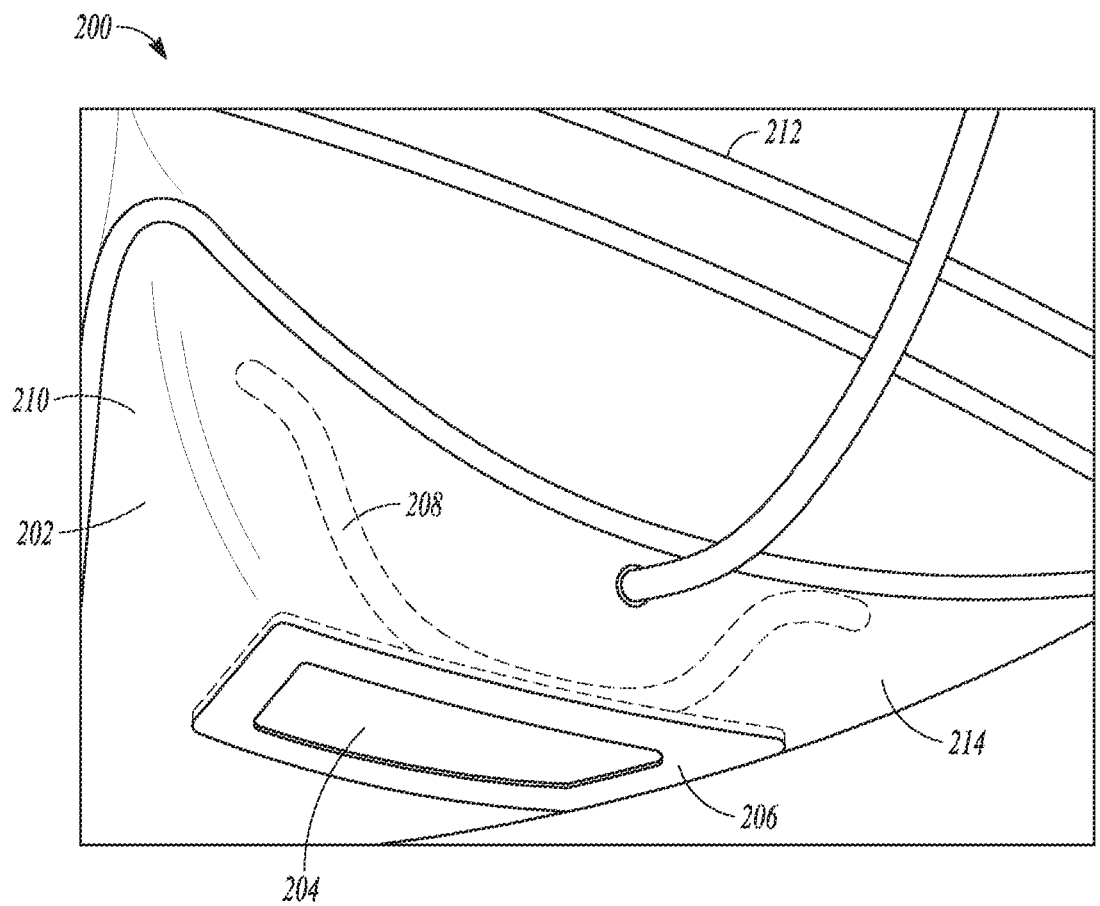
FIG. 2 illustrates an elevational view of a top portion of a system, as constructed in accordance with at least one embodiment.
Figure 3:
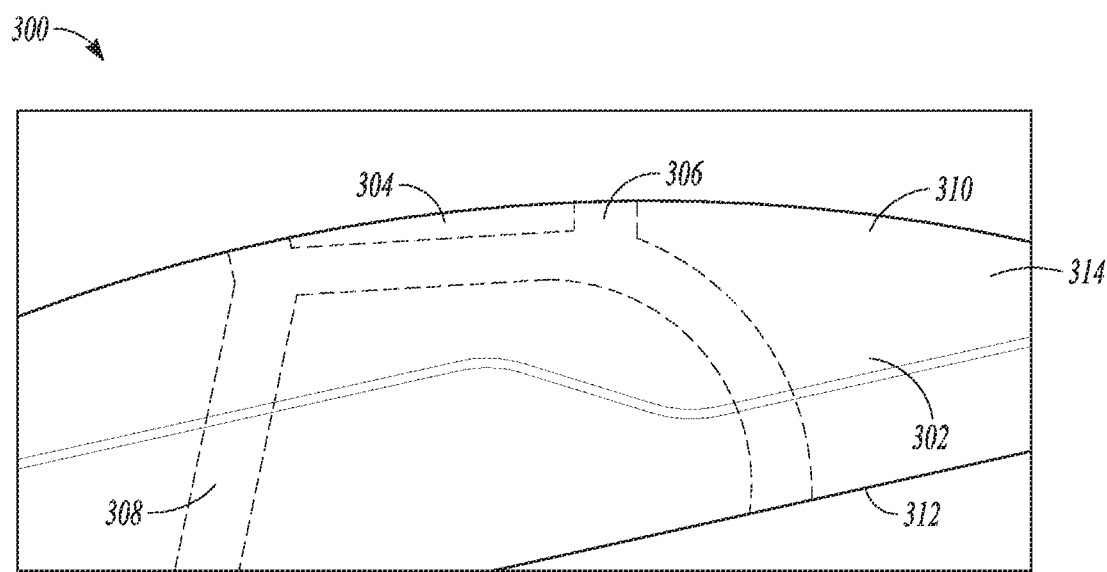
FIG. 3 illustrates a side view of a top portion of a system, as constructed in accordance with at least one embodiment.

FIGS. 2 and 3 illustrate elevational and side views, respectively, of a top portion 214, 314 of a system 200, 300. Each system 200, 300 can include a flexible container 202, 302 having a front side 210, 310 and a back side 212, 312, a membrane 204, 304, a membrane frame 206, 306 and at least one column member 208, 308.

Containers without sidewalls can include contents that contact a membrane resulting in the material freezing against the membrane. The material can then dry against and plug up the membrane resulting in reduction of a lyophilization rate and a reduced usefulness of the system. As such, it is important to prevent the membrane from contacting container contents (e.g., biological material). Advantageously, the at least one column member 208, 308 can maintain one or more of the front side 210, 310 of the flexible container 202, 302, the membrane 204, 304, and the membrane frame 206, 306 above any contents during lyophilization. The at least one column member 208, 308 can be sufficiently stiff to support the front side 210, 310, the membrane 204, 304, and the membrane frame 206, 306 above the contents, yet sufficiently deformable or pliable to collapse subsequent to lyophilization, as sequentially illustrated in FIGS. 9-11. The at least one column member 208, 308 can have various linear or non-linear configurations, including a bent leg shape, a helical spring shape or a tubular shape.

Figure 4:
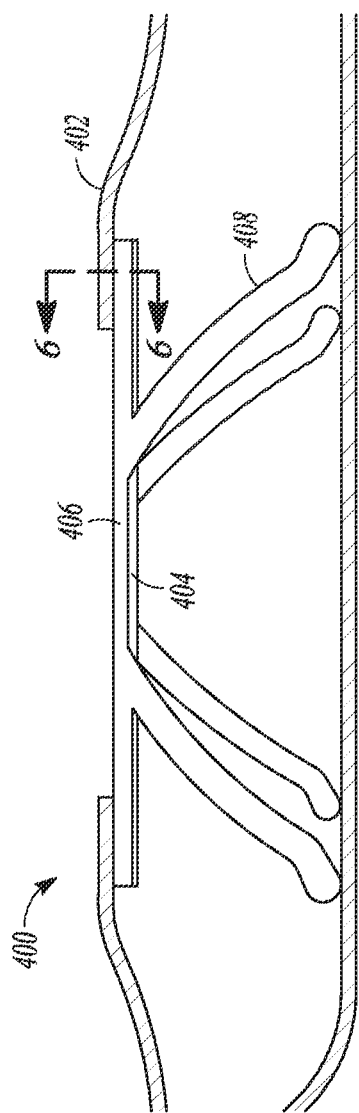
FIG. 4 illustrates a cross-sectional view of a system, such as a cross-section taken along line 4-4 of FIG. 1.
Figure 5:
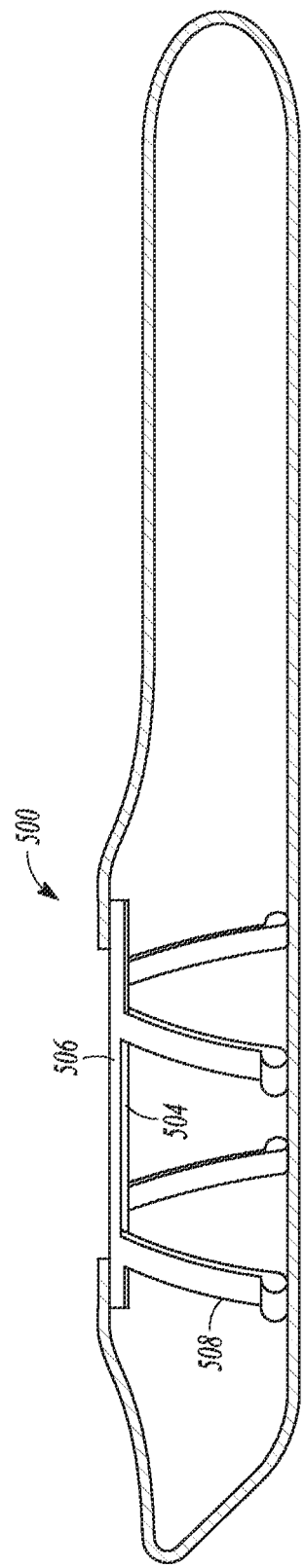
FIG. 5 illustrates a cross-sectional view of the system, such as a cross-section taken along line 5-5 of FIG. 1.

FIGS. 4 and 5 illustrate cross-sectional views of a system 400, 500, such as cross-sections taken along lines 4-4 and 5-5 of FIG. 1, respectively. As partially shown in FIG. 4, a widthwise cross-section of the flexible container 402 can assume an ellipsoid shape in the absence of sidewalls. Flexible containers without sidewalls can be efficiently and economically manufactured using a single, outer perimeter sealing step. With the addition of at least one column member 408, 508, a membrane 404, 504 and a membrane frame 406, 506 can be supported above any material contents, as shown in FIGS. 4 and 5.

Figure 6:
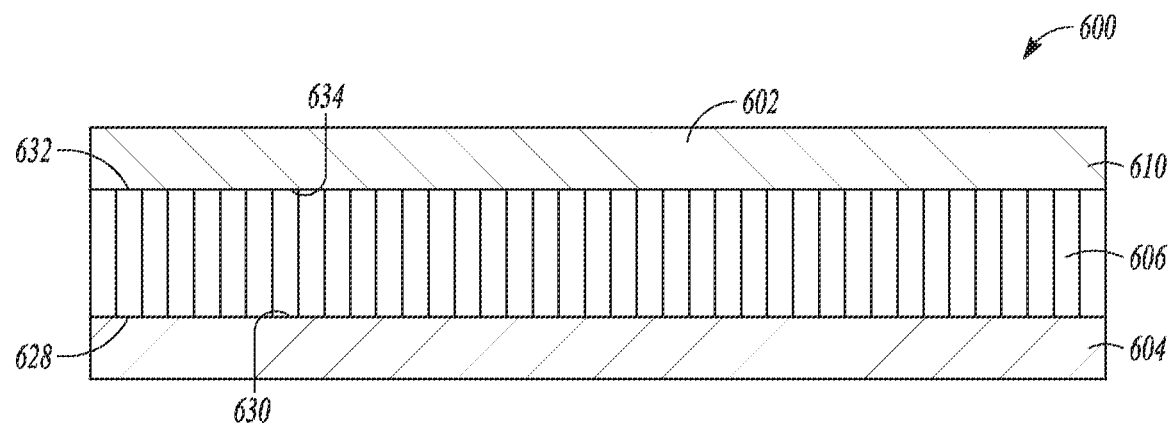
FIG. 6 illustrates a cross-sectional view of a membrane, a membrane frame and a flexible container, such as a cross-section taken along line 6-6 of FIG. 5.

FIG. 6 illustrates a cross-sectional view of a system 600, such as a cross-section taken along line 6-6 of FIG. 4. The system 600 can include a front side 610 of a flexible container 602, a membrane 604 and a membrane frame 606. To assemble these portions of the system 600, the membrane frame 606 can be laid on top of the membrane 604, and the front side 610 of the flexible container 602 can be laid on top of both the membrane 604 and the membrane frame 606. The three layers can then be adhesive coupled or bonded with a heat-sealer, an ultrasonic welder, or an RF welder to bond a bottom surface 628 of the membrane frame 606 to a top surface 630 of the membrane and a top surface 632 of the membrane frame 606 to a bottom surface 634 of the front side 610 of the flexible container 602. For aseptic reasons, it can be important that the seals between the membrane 604, the membrane frame 606 and the flexible container 602 are fluid and vapor tight.

The system 600 can include one or more magnetic members or one or more hook members coupled to or integrated with the flexible container 602, the membrane 604 or the membrane frame 606. The magnetic or hook members can interact with an external magnetic member or an external support to maintain the membrane 604 above any material contents within the flexible container. The one or more magnetic or hook members can be used alone or in conjunction with the at least one column member described elsewhere in this patent document.

Figure 7:
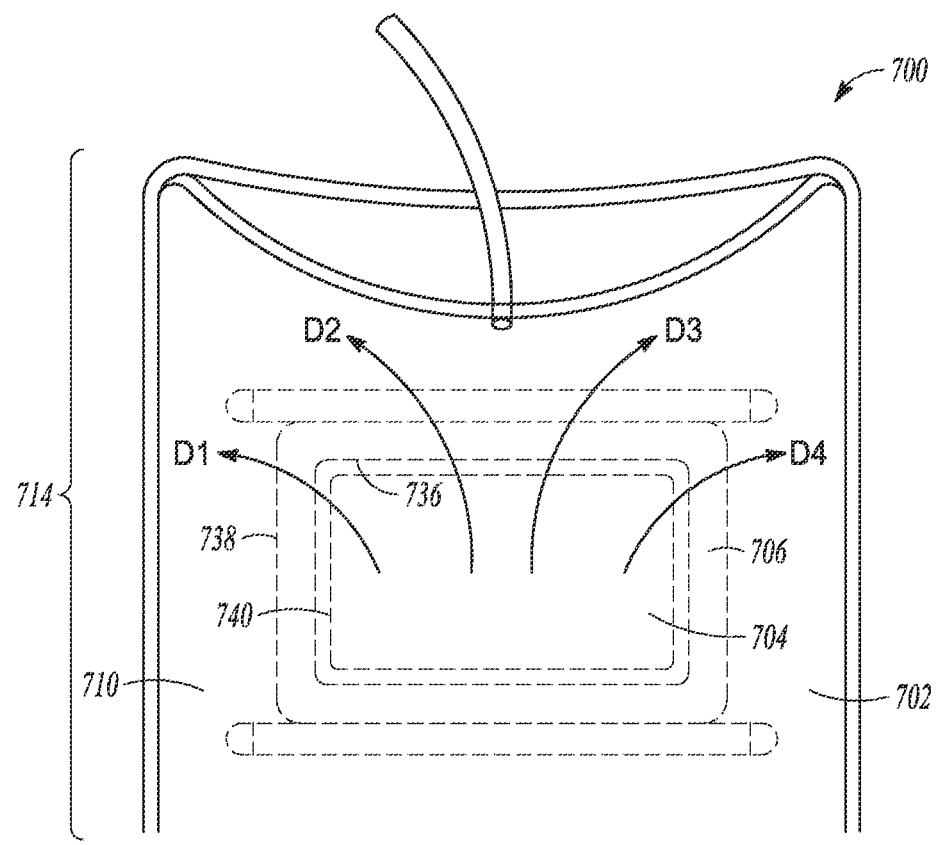
FIG. 7 illustrates an elevational view of a top portion of a system, as constructed in accordance with at least one embodiment.

FIG. 7 illustrates an elevational view of a top portion 714 of a system 700. The system 700 can include a front side 710 of a flexible container 702, a membrane 704, and a membrane frame 706. The front side 710 of the flexible container 702 and the membrane 704 can be supported along their peripheries by the stiffer membrane frame 706. The membrane 704 can be sized such that its outer periphery is larger than an inner periphery 736 of the membrane frame 706 and smaller than, or equal to, an outer periphery 738 of the membrane frame 706. A void in the front side 710 of the flexible container 702 can have a periphery that is smaller than the outer periphery 738 of the membrane frame 706 and larger than, or equal to, the inner periphery 736 of the membrane frame 706.

During lyophilization, solvent vapor can pass out of the flexible container 702 through the membrane 704 in a variety of directions, such as one or more of $D_1$, $D_2$, $D_3$, and $D_4$. Particulate biological material, for example, can be retained within the flexible container 702 and contamination from the container's surroundings can be excluded by the aseptic barrier properties of the membrane 704. The membrane 704 can be made of any vent material that is solvent vapor permeable and that provides effective resistance to bacterial penetration. Aseptic papers, woven or non-woven polymeric fabrics, such as spun-bonded polyolefin, porous polymer membranes, such as PTFE and ePTFE, glass fiber, nitrocellulose, mixed cellulose esters, polyvinylidene fluoride (PVDF), polyethersulfone, polycarbonate, nylon, polypropylene, and PVC are examples. PTFE can be a preferred membrane material based on its combination of hydrophobicity and solvent vapor flow for a given nominal pore size.

Optionally, a removable cover 740 (shown in phantom) can be added to an upward-facing surface of the membrane 704. The removable cover 740 can protect the membrane 704 during any processing before lyophilization. The removable cover 740 can include a tab that extends beyond the inner 736 or outer 738 peripheries of the membrane frame 706 to allow a user to grasp and remove the cover to expose the membrane 704.

Figure 8:
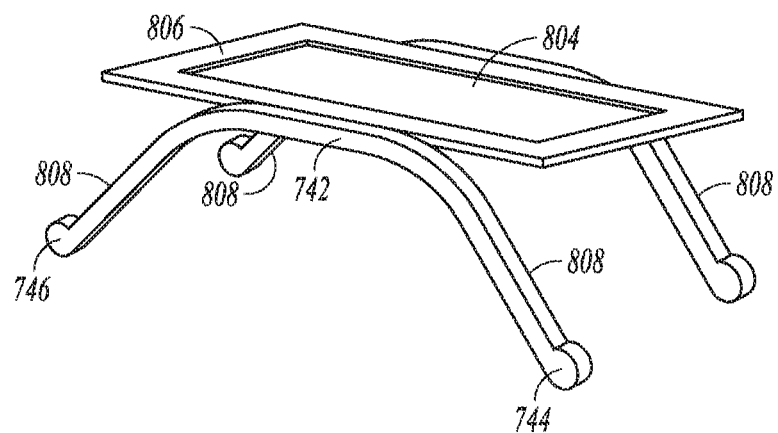
FIG. 8 illustrates a front elevational view of a membrane, a membrane frame, and at least one column member in a relaxed configuration, as constructed in accordance with at least one embodiment.

FIG. 8 illustrates a front elevational view of a membrane 804, a membrane frame 806 and at least one column member 808 in a relaxed configuration. The at least one column member 808 can be sized, shaped and positioned to support the membrane 804 and the membrane frame 806 above any contents (e.g., biological material) within a flexible container. The at least one column member 808 can include a first end 742 engaged with the membrane frame 806 and a second end 744 or a third end 746 in contact with a surface of a back side of the flexible container. Alternatively, the at least one column member 808 can be configured to externally support the membrane 804 and the membrane frame 806 above any contents within the flexible container. In such an example, the second end 744 or the third end 746 of the at least one column member 808 can contact a surface external to the flexible container.

In the example shown, the at least one column member 808 can define a U-shape, with the curvature of the U-shape engaged with the membrane frame 806. The at least one column member 808 can be separate from or integral with the membrane frame 806. In various examples, the at least one column member 808 can be molded from a thermoplastic, such as acrylonitrile butadiene styrene (ABS), PVC or polypropylene or a metallic material.

Figure 9:
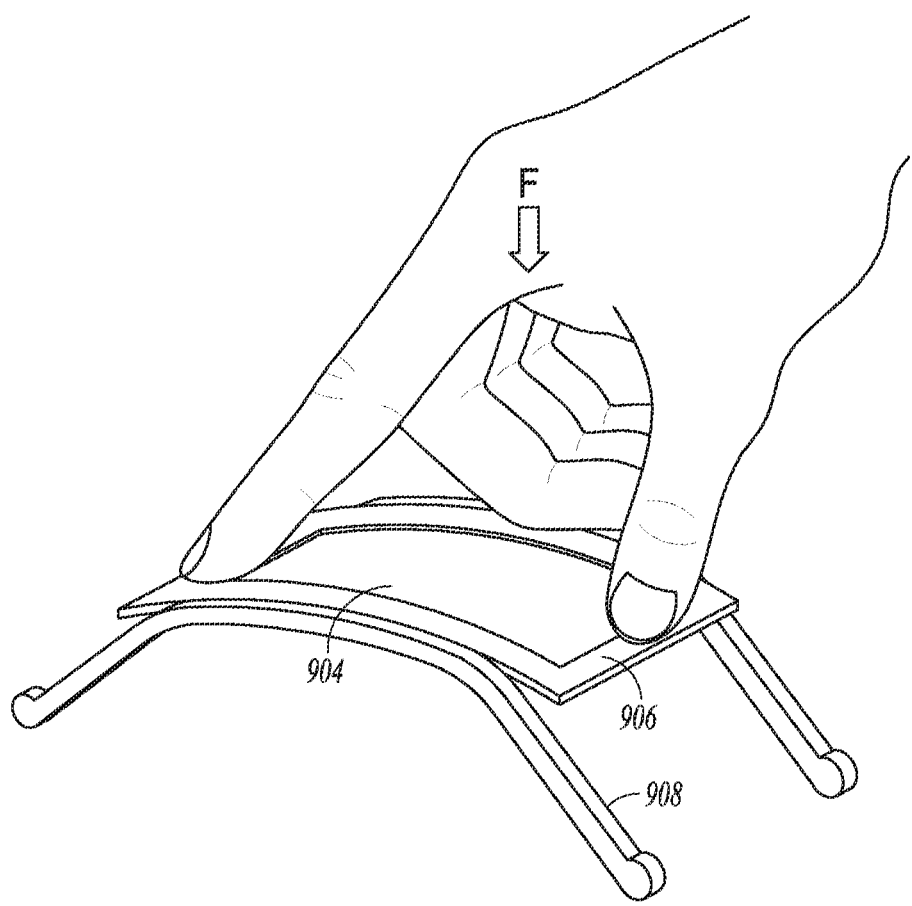
FIGS. 9-11 illustrate sequential perspective views of a membrane, a membrane frame, and at least one column member subjected to a force F in a downward direction, as constructed in accordance with at least one embodiment.
Figure 10:
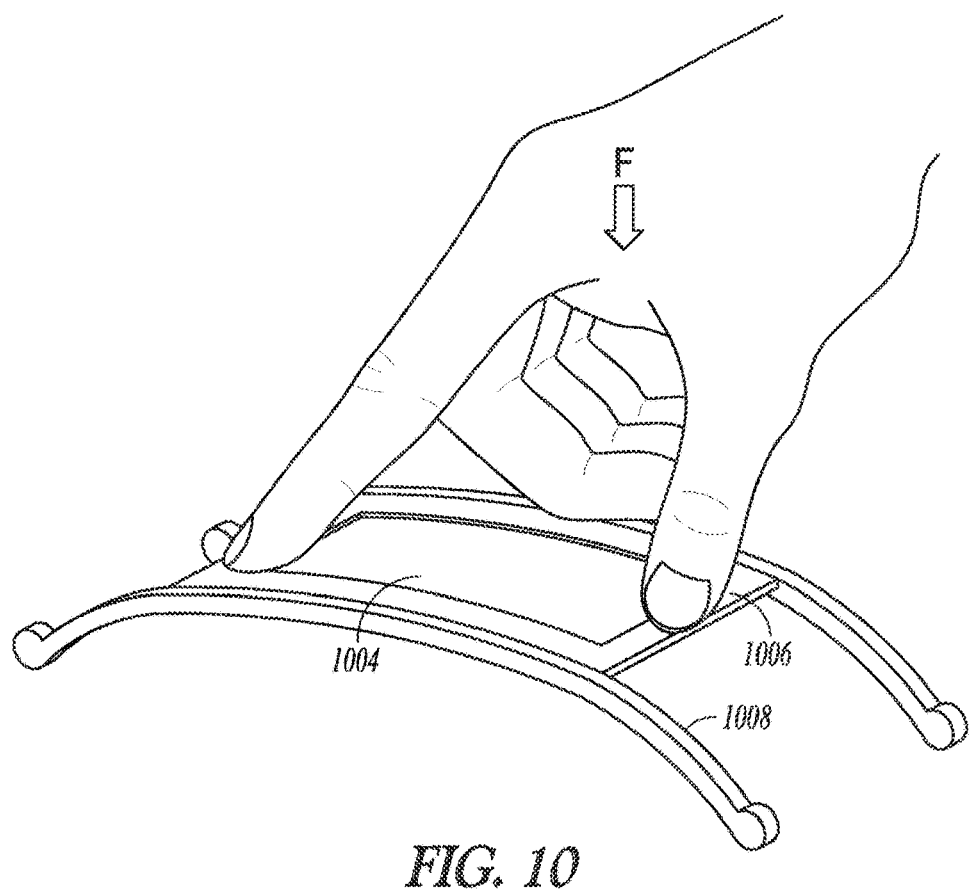
Figure 11:
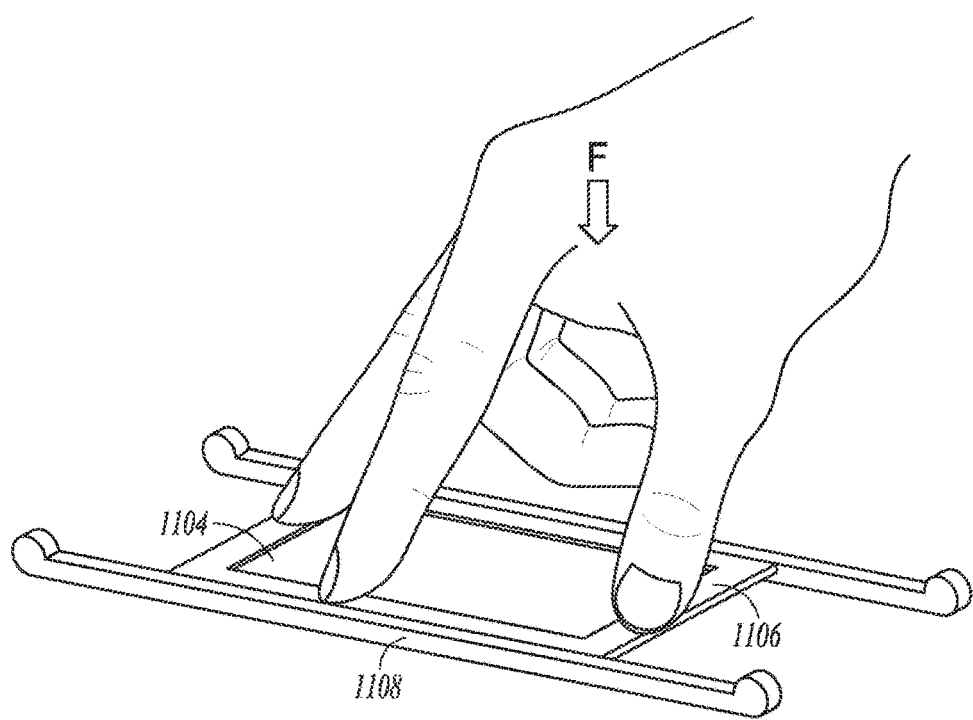

FIGS. 9-11 illustrate sequential perspective views of a membrane 904, 1004, 1104, a membrane frame 906, 1006, 1106 and at least one column member 908, 1008, 1108 subjected to a downward force F. As shown, the at least one column member 908, 1008, 1108 can include a plurality of column members configured to change shape or position relative to the membrane frame 906, 1006, 1106 upon application of the downward force F. In an example, the plurality of column members 908, 1008, 1108 can be deformed into a planar orientation with the membrane frame 906, 1006, 1106, as shown in FIG. 11. Optionally, the at least one column member 908, 1008, 1108 can include a recess that allows a portion of the column member to break-off upon application of the downward force F. Through the breaking-off of the portion of the column member, the membrane frame 906, 1006, 1106 can contact a surface of a back side of a flexible container.

Figure 12:
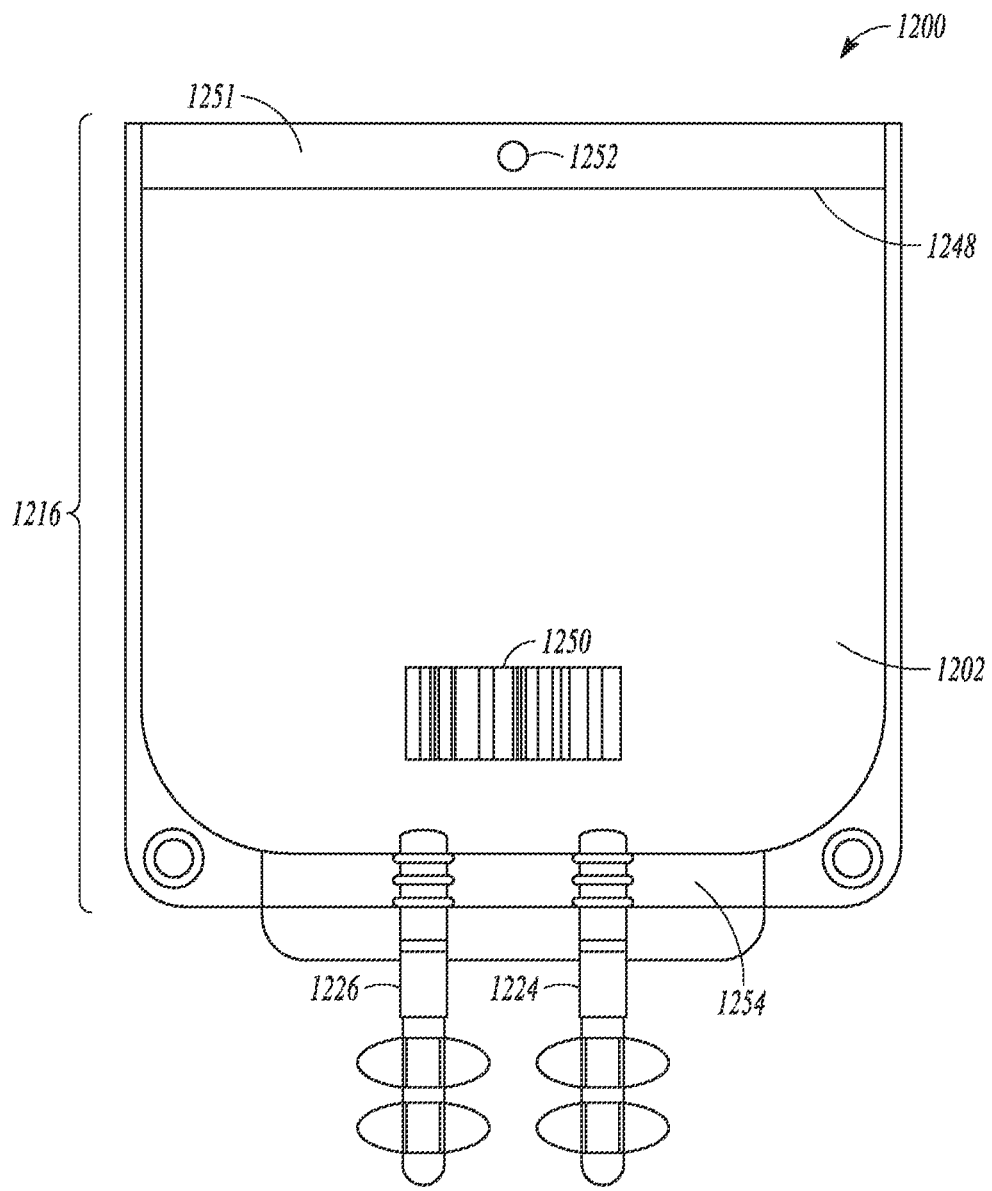
FIG. 12 illustrates an elevational view of a bottom portion of a system, as constructed in accordance with at least one embodiment.

FIG. 12 illustrates an elevational view of a bottom portion 1216 of a system 1200. The system 1200 can include a flexible container 1202, a reconstitution port 1224 and an application port 1226. The flexible container 1202 can contain a freeze-dried material, such as freeze-dried biological material. In an example, the freeze-dried biological material is a blood plasma unit, which can include about 250-270 mL of blood plasma from a single donor. The blood plasma unit, for example, can be dried so that its moisture content is below about 5% weight/weight (w/w), which can be stored, transported, and later reconstituted and applied to a patient.

An advantage of a freeze-dried material is the possible storage for a comparably longer period of time at temperatures of about 0° C. (Celsius) up to room temperature and beyond, combined with a reduced weight due to reduced water content. Although a freeze-dried material requires reconstitution, the advantages are predominant in certain situations, especially in emergency medicine under difficult treatment conditions (e.g., in combat treating wounded warriors or in ambulances and helicopters treating civilian trauma) when the thawing of frozen biological material to be applied is time-consuming (e.g., around 15 minutes or more) and inconvenient.

Freeze-dried biological material, for example, can be packaged for storage in a container that presents a barrier to solvent vapor transmission, thereby minimizing the opportunity of rehydrating the dried contents. Advantageously, the flexible container 1202 can be sealed 1251 (e.g., using heat sealing, RF welding or ultrasonic welding) near an end 1248 of the bottom portion 1216, which is located opposite the reconstitution 1224 and application 1226 ports, after the dried contents are entirely moved to the bottom portion 1216. The size and configuration of the bottom portion 1216 of the flexible container 1202 can maintain the freeze-dried biological material prior to its reconstitution in a moisture-free environment, thereby accommodating long-term storage (e.g., 2 to 3 years at refrigerated temperatures and a plurality of months at room temperature) and retaining its desired qualities for transfusion.

In addition to storing the freeze-dried biological material, the bottom portion 1216 of the flexible container 1202 can be sized and configured to receive reconstitution liquid, such as about 250 mL of water. In this way, the bottom portion 1216 of the flexible container 1202 can provide a single receptacle to store freeze-dried contents, rehydrate the dried contents, and apply the rehydrated product to a patient.

The reconstitution 1224 and application 1226 ports can be thermally, ultrasonically, or adhesively coupled or RF welded to an outer perimeter of the second portion 1216 and oriented to be in fluid communication with an interior of the flexible container 1202 and its contents. The ports 1224, 1226 can include a diaphragm or other piercable membrane to maintain material sterility and prevent inadvertent flow out of the flexible container 1202. To ensure that the material within the flexible container 1202 can easily and completely empty out of the container, at least the application port 1226 can be positioned at a bottom end 1254 of the second portion 1216, opposite the seal 1251, when the container is suspended by a hang lumen 1252 located near the top end 1248.

Bar coding and tagging 1250 can be applied to the bottom portion 1216 of the flexible container 1202. The bar coding and tagging 1250 can, for example, reflect biological material identification, including blood plasma source, blood type, date of collection, etc., carried by the bottom portion 1216.

First aid is critical for the survival of a patient that has suffered a serious injury, such as a trauma victim. For example, initial treatment of a severely wounded warrior in a combat situation can often mean the difference between life and death. While it is necessary to treat wounds and stop the bleeding of a patient, it is also important to ensure that the patient's body is capable of properly functioning. Thus, it is necessary to take steps to ensure that the patient's body is properly hydrated after losing fluids due to the wounds. The present system and method address this issue.

Using existing technology, fluids within a patient are typically replenished by intravenously delivering saline. While effective, research has indicated that delivery of blood plasma to the patient is even more effective in replenishing fluid to the patient. Processing, storage, and delivery of the blood plasma can be critical to preventing contamination of the plasma. An ideal way of delivering blood plasma is to store it in a freeze-dried form and reconstitute the blood plasma at the time it is administered to the patient.

Figure 13:
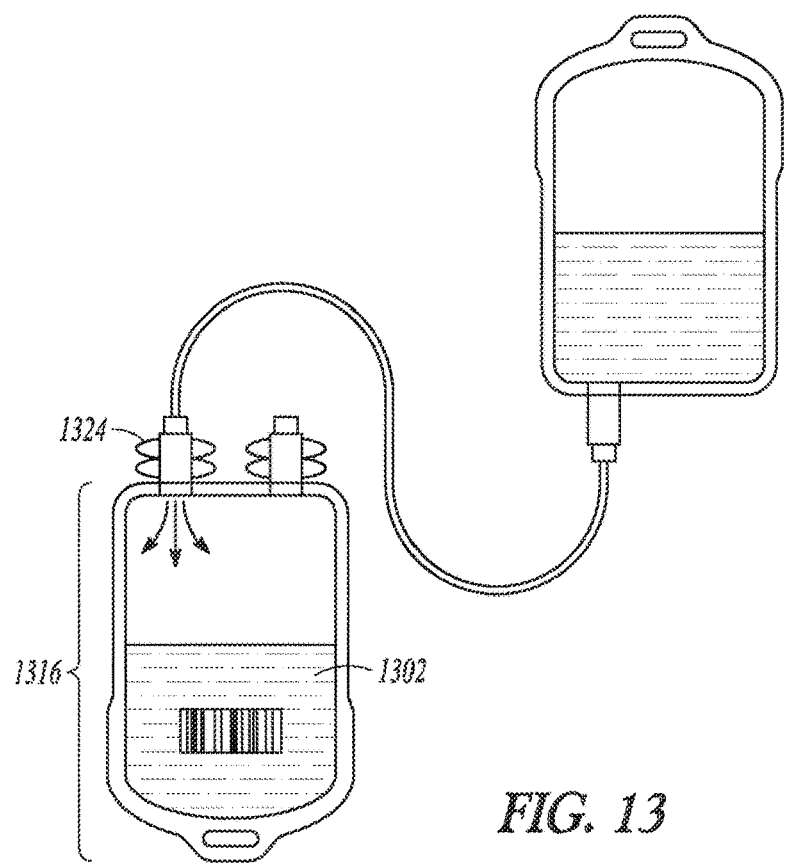
FIG. 13 illustrates a schematic view of reconstituting a freeze-dried material, as constructed in accordance with at least one embodiment.

FIG. 13 illustrates a schematic view of reconstituting a freeze-dried biological material, such as blood plasma. The freeze-dried biological material can be stored in a bottom portion 1316 of a flexible container 1302. This portion 1316 of the flexible container 1302 can be sized to receive a reconstitution liquid (e.g., about 250 mL of water) through a reconstitution port 1324 for mixing with the freeze-dried biological material. In use, a needle or IV spike sized and configured to puncture a diaphragm or other piercable membrane within the reconstitution port 1324 can be used to establish fluid communication between the reconstitution liquid and the freeze-dried biological material. The freeze-dried biological material and the reconstitution liquid can then be passed back and forth within the flexible container 1302 until a desired degree of mixing occurs, at which time the mixture is ready for transfusion. More particularly, a caregiver can proceed to squeeze opposing ends or sides of the bottom portion 1316 of the flexible container 1302 to move and mix the freeze-dried biological material and the reconstitution liquid.

Figure 14:
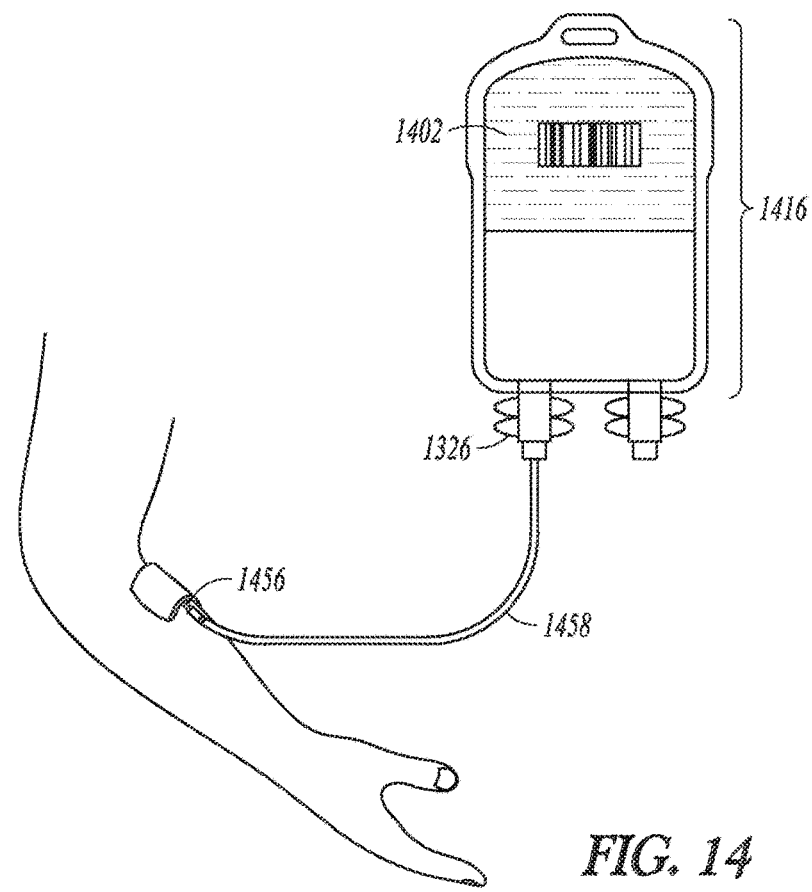
FIG. 14 illustrates a schematic view of applying a reconstituted material to a patient, as constructed in accordance with at least one embodiment.

FIG. 14 illustrates a schematic view of applying a reconstituted biological material, such as reconstituted blood plasma, to a patient. The reconstituted material can be administered by way of an application port 1326. An application set can include a phlebotomy needle 1456 for insertion into a vein, aseptic tubing 1458 connecting the needle 1456 to a bottom portion 1416 of a flexible container 1402 and its reconstituted biological material contents, and a needle or IV spike to puncture a diaphragm or other piercable membrane within the application port 1326.

Figure 15:
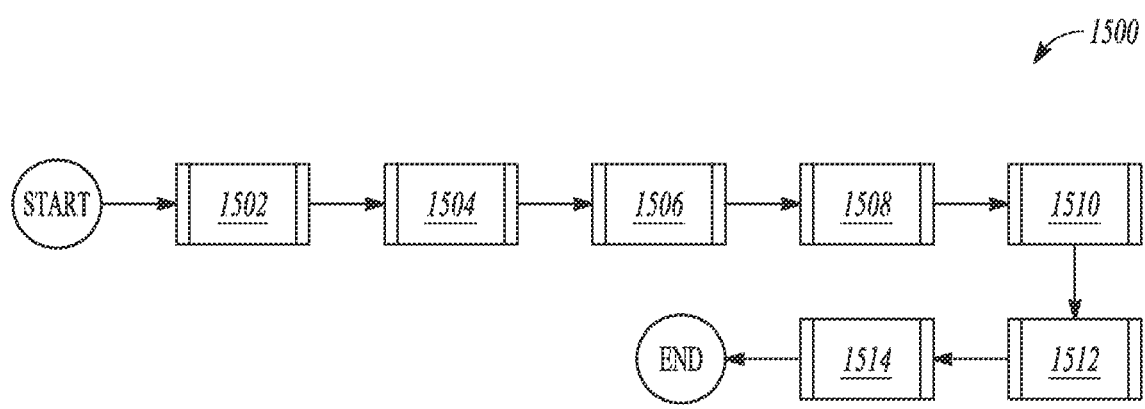
FIG. 15 illustrates a method of filling a flexible container with a material, freeze-drying the material, and packaging the material for later use, as constructed in accordance with at least one embodiment.

FIG. 15 illustrates a method 1500 of filling a flexible container with a biological material, such as blood plasma, freeze-drying the blood plasma, and packaging the blood plasma for later use.

In operation 1502, a blood plasma source unit can be obtained. Blood plasma can be obtained from a single donor or a pooling of donors by collecting a unit of whole blood from the donor(s) in a closed system collection bag, followed by centrifugal separation of the blood plasma and its collection in an integrally connected transfer bag. The blood plasma can be obtained in individual units of about 270 mL, for example, shipped frozen and stored in a 20° C. freezer. Identification information, maintained by bar coding or other tagging means, can be supplied with each individual donor blood plasma unit for traceability purposes.

In operation 1504, the blood plasma source unit can be prepared for freeze-drying. The blood plasma unit can be removed from the freezer and any associated packaging can be discarded. The blood plasma unit can be transferred into a plasma thawing unit and allowed to thaw. The thawed blood plasma unit can be bar code scanned, for example, and an identification tag can be made. The identification tag can include unit specific information to maintain traceability of the blood plasma.

In operation 1506, the blood plasma can be transferred into a water-impermeable, vapor-permeable, aseptic, sealable flexible container. The flexible container and the blood plasma source unit can be coupled together using a material entry port in the form of aseptic tubing. The blood plasma can be transferred through the aseptic tubing using positive pressure. The total mass of the transferred blood plasma can be about 270 g. Once the blood plasma has been transferred, a portion of the aseptic tubing can be thermally or otherwise sealed to protect the unit from contamination.

The flexible container can include a first side incorporating a membrane and a second side, which are spaced from one another by a membrane frame and at least one column member. The identification tag made in operation 1504 can be attached to the flexible container.

In operation 1508, the filled flexible container can be placed on a horizontally-oriented freeze-dryer tray such that the membrane is on top, facing upward, and the container can be freeze-dried. This placement of the membrane can allow for controlled and consistent conduction during the freeze-drying process, as air or solvent vapor can escape the flexible container through the membrane. Optionally, the filled flexible container can be placed on a vertically-oriented freeze-dryer tray and the membrane can be incorporated at any location of an upper, first portion of the container. After placing the flexible container on a shelf in a freeze-dryer chamber, the shelf can be cooled using a heating and cooling unit to preliminarily freeze the article to be freeze-dried. Alternatively, the filled flexible container to be freeze-dried can be pre-frozen using a separate unit (e.g., a −60° C. freezer) and arranged on the shelf.

Next, the pressure inside the freeze-dryer can be reduced to sublimation dry the contents of the flexible container. The pressure inside the freeze-dryer can be reduced to about 100 mTorr to sublimate ice to solvent vapor without going through a liquid state. During the sublimation drying step, the shelf within the freeze-dryer chamber can be maintained at an adequate temperature for supplying a latent heat of sublimation using the heating and cooling unit.

Solvent vapor released from the contents of the flexible container by sublimation can be captured by a cold trap or other type of capturing unit. In the case of using a cold trap (condenser unit), the cold trap can be cooled to a temperature below the temperature of the contents, and preferably to a temperature that demonstrates a solvent vapor pressure sufficiently lower than the solvent vapor pressure of water at the temperature of the contents (for example, −50 to −60° C.).

In an example, the freeze-drying cycle can include cooling the shelf to less than about −40° C., loading the filled flexible container and its tray onto the shelf, initiating a six or seven day freeze-drying cycle including a four or five day primary drying cycle and a two day secondary drying cycle, ending the secondary drying cycle and break vacuuming using extra dry, high purity carbon dioxide, removing the freeze-dried filled flexible container and placing it in a desiccated storage chamber.

In operation 1510, the freeze-dried blood plasma can be moved to a portion of the flexible container spaced from the membrane, the membrane frame, and the at least one column member and then sealed. Specifically, the flexible container can be removed from the desiccated storage chamber and its freeze-dried blood plasma contents can be moved to a portion of the flexible container including two ports—a reconstitution port and an application port. Prior to making a seal of about 1 inch, for example, across a midline of the flexible container, for example, a downward force can be applied to the membrane frame to cause the at least one column member to collapse. A portion of the seal can be cut through and a first portion of the flexible container, which includes the membrane, the membrane frame and the at least one column member, can be discarded in a biohazard container. A hang lumen can be added to the remaining portion of the formed seal.

In operation 1512, the remaining portion of the formed seal can optionally be cleaned. In an example, the non-discarded second portion of the flexible container can be inverted such that the seal, positioned opposite the reconstitution and application ports, can be immersed into 10% bleach or another cleansing solution. This cleansing can ensure that no blood plasma is on a surface of the seal. After the seal is allowed to soak for about 10 minutes, the second portion of the flexible container can be rinsed with deionized water.

In operation 1514, the second portion of the flexible container can be labeled and packaged. The bar code printed on the identification tag in operation 1504 can be scanned and three labels with associated information can be printed. The three labels can be placed on the second portion of the flexible container, which includes the freeze-dried plasma, an external foil containment pouch and a final packaging. A first label can be placed on the second portion of the flexible container and the original identification tag can be removed. The labeled second portion of the flexible container can then be placed into the external foil containment pouch and packaged. The second portion of the flexible container can be packaged in a military grade ruggedized container with 250 mL of reconstitution liquid, for example, and aseptic tubing for transferring the reconstitution liquid to the flexible container.

Closing Notes:

Existing systems and methods for freeze-drying, repackaging and using freeze-dried contents suffer from concerns of contamination, expense and lack of convenience. Advantageously, the present subject matter provides an economical and efficient system and method for protecting material from contamination through the steps of filling, freeze-drying, packaging, storing and use. The system and method can be designed for blood products, such as blood plasma, and can be adoptable to other materials that would benefit from the design and features of the invention.

The above Detailed Description includes references to the accompanying drawings, which form a part of the Detailed Description. The Detailed Description should be read with reference to the drawings. The drawings show, by way of illustration, specific embodiments in which the present system and method can be practiced. These embodiments are also referred to herein as "examples." While certain examples are described with respect a blood plasma biological material, it is to be appreciated that the present disclosure is equally applicable to non-blood related biological materials, as well as non-biological materials.

The above Detailed Description is intended to be illustrative, and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms, certain definitions shall be applied, unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, 3 to 4.25, etc.). The term "patient" is intended to include mammals, such as for human or veterinary applications.

In the appended claims, the terms "including" and "in which" are used as the plain-English equivalents of the respective terms "comprising" and "wherein." Also, in the following claims, the terms "including" and "comprising" are open-ended, that is, a system, kit, or method that includes features or components in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system for freeze-drying and packaging a heat-sensitive substance, comprising:
   a container comprising a sealable material, the container having a first portion and a second portion wherein the first portion and the second portion are configured to pass the substance from within the first portion to within the second portion;
   a membrane attachable to a surface of the first portion and configured to transmit air or solvent vapor out of, and resist liquid or contaminant passage into, the first portion; and
   at least one port to allow for an introduction or a withdrawal of a liquid into or out of the container.

2. The system of claim 1, wherein the first portion and the second portion are defined as separate portions at an intermediate location of the container.

3. The system of claim 2, wherein the container is sealable at the intermediate location.

4. The system of claim 2, wherein the container is configured to be sealed at the intermediate location after the substance has passed into the second portion.

5. The system of claim 4, wherein the first portion and the second portion are configured to be detached after the container is sealed at the intermediate location.

6. The system of claim 1, further comprising a frame within the first portion, the frame coupled to the surface of the first portion.

7. The system of claim 6, further comprising at least one support member engaged with the frame and configured to support the frame.

8. The system of claim 7, wherein the at least one support member is integral with the frame.

9. The system of claim 7, wherein the at least one support member defines a U-shape, with the curvature of the U-shape engaged with the frame.

10. The system of claim 6, further comprising one or more magnetic or hook members coupled to or integrated with the first portion or the frame and configured to interact with an external magnetic member or an external support.

11. The system of claim 1, further comprising a removable cover protecting the membrane.

12. The system of claim 1, further comprising the heat-sensitive substance.

13. The system of claim 12, wherein the heat-sensitive substance comprises a biological material.

14. The system of claim 12, wherein the heat-sensitive substance comprises a non-biological material.

15. The system of claim 1, wherein the at least one port includes at least one port in each of the first portion and the second portion.

16. The system of claim 15, wherein the at least one port in the second portion is a reconstitution port that allows for the introduction of the liquid into the container.

17. The system of claim 1, wherein the membrane includes a membrane material selected from a porous polymer, a woven polymeric fabric, a non-woven polymeric fabric, glass fiber, or cellulose.

18. The system of claim 1, wherein the membrane comprises polytetrafluoroethylene.

19. The system of claim 1, wherein the sealable material comprises an inert medical grade plastic material.

20. The system of claim 1, wherein the sealable material comprises polyvinyl chloride, polypropylene, or high density polypropylene.

* * * * *